(12) United States Patent
Takaku et al.

(10) Patent No.: US 6,284,870 B1
(45) Date of Patent: *Sep. 4, 2001

(54) GAMMA RETINOIC ACID RECEPTOR (75) Inventors: Fumimaro Takaku; Takashi Ishikawa; Michio Imawari, all of Tokyo (JP); Ronald Mark Evans; Kazuhiko Umesono, both of La Jolla, CA (US)

(73) Assignees: The Salk Institute for Biological Studies, La Jolla, CA (US); Sloan-Kettering Institute for Cancer Research, Rye, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/486,325

(22) Filed: Jun. 7, 1995

Related U.S. Application Data (60) Continuation of application No. 08/100,039, filed on Jul. 30, 1993, now Pat. No. 5,530,094, which is a division of application No. 07/370,407, filed on Jun. 22, 1989, now Pat. No. 5,260,432.

(51) Int. Cl.[7] .................................................. C07K 5/00
(52) U.S. Cl. .............................................. 530/350; 935/11
(58) Field of Search .................................. 530/350, 380, 530/324, 500, 826, 846; 930/180; 435/69.1, 320.1, 240.2, 252.3; 935/11

(56) References Cited

U.S. PATENT DOCUMENTS

| | | | |
|---|---|---|---|
| 5,260,432 | * 11/1993 | Takaku et al. | 536/23.5 |
| 5,530,094 | * 6/1996 | Takaku et al. | 530/324 |

OTHER PUBLICATIONS

Brand et al., Nature 332(6167):850–853, Apr. 1988.*

* cited by examiner

*Primary Examiner*—Scott W. Houtteman
(74) *Attorney, Agent, or Firm*—Gray, Cary, Ware & Freidenrich LLP; Stephen E. Reiter; Stanley H. Kim (57) ABSTRACT

A novel gamma retinoic acid receptor is disclosed. The novel receptor is encoded for by cDNA carried on plasmid pGEM-hRARγ, which has been deposited with the American Type Culture Collection for patent purposes. Chimeric receptor proteins are also disclosed. The chimera contain at least one functional domain from the new gamma retinoic acid receptor.

4 Claims, 4 Drawing Sheets

FIG. 1-1

```
  1                                           GAATTCGGCTCAACCTGACCCAGTATGTAGAAGCCAGTCTC
 43 TGCAGGCGGCCAGCGGGACTTTTGGAGGCCCAGTGGGCAGGCCAGGGGCAGGGGTACGGGAGCCTCCCAGGCTGGGGCA
121 GTGGGCATGGGCAGGGGCTGTGTGGCTGAAGACCTCGCCGCCCACTGCAGACCCCAGGGGACTCTCACACCGCAGCTGCC

200 ATG GCC ACC AAT AAG GAG CGA CTC TTT GCG GCT GGT GGG CCT GGA TCT GGC TAC
  1 Met Ala Thr Asn Lys Glu Arg Leu Phe Ala Ala Gly Gly Pro Gly Ser Gly Tyr

260 CCA GGG GCA GGT TTC CCC TTC GCC TTC CCA GGG GCA CTC AGG GGG TCT CCG CCT TTC GAG
 21 Pro Gly Ala Gly Phe Pro Phe Ala Phe Pro Gly Ala Leu Arg Gly Ser Pro Pro Phe Glu

320 ATG CTG AGC CCT AGC TTC CGG GGC CTG GGC CAG CAG CCT GAC CTC CCC AAG GAG ATG GCC TCT
 41 Met Leu Ser Pro Ser Phe Arg Gly Leu Gly Gln Gln Pro Asp Leu Pro Lys Glu Met Ala Ser

380 CTG TCG GAG ACA CAG AGC AGC ACC TCA GAG ATG ATG GTG CCC AGC TCG TCT CCC
 61 Leu Ser Val Glu Thr Gln Ser Ser Thr Ser Glu Met Met Val Pro Ser Ser Ser Pro

440 CCT CCG CCT TAC GTC CGG TAC AAG CTG TGC TTC GTG AAT GAC AAG TCC TCT GGC TAC
 81 Pro Pro Pro Tyr Val Arg Tyr Lys Leu Cys Phe Val Asn Asp Lys Ser Ser Gly Tyr

500 CAC TAT GGG TCT AGC GTC TGT TGT GAA GGC TTT ATC ATC AGC CGA AAG AAG CAG AAG
101 His Tyr Gly Val Ser Val Cys Cys Glu Gly Phe Ile Ile Ser Arg Lys Gln Lys

560 AAC ATG GTG TAC ACG TGT CAC CGC GAC AAA AAC ATC GTG GGC GTG AAG GTG AAT
121 Asn Met Val Tyr Thr Cys His Arg Asp Lys Asn Ile Val Gly Val Lys Val Asn

620 CGC TGC CAG TAC TGC CGG CTA CAG AAG TGC TTC GAA GTG GAA GTG TCC ATG GAA GCT
141 Arg Cys Gln Tyr Cys Arg Leu Gln Lys Cys Phe Glu Val Glu Val Ser Lys Glu Ala

680 CGA AAT GAC CGG AAC AAG AAG AAA CAG GAA GTG CCT TCA GGG GAA GAC TAT
161 Arg Asn Asp Arg Asn Lys Lys Lys Gln Glu Val Pro Lys Ser Met Gly Glu Asp

740 GAG CTG AGC CTT GAA TTA GAA GAG CTC ATC ACC AAG GTC AGC AAA GCC CAT CAG GAG ACT
181 Glu Leu Ser Pro Leu Glu Glu Leu Ile Thr Lys Val Ser Lys Ala His Gln Glu Thr
```

FIG. 1-2

```
 800  TTC CCC TCG CTC TGC CAG GGC AAG TAT ACC AAC ACG AGT GCA GAC CAC CGC GTG
 201  Phe Pro Ser Leu Cys Gln Gly Lys Tyr Thr Asn Thr Ser Ala Asp His Arg Val

860  CAG CTG GAT CTG GGG CTG TGG GAC AAG TTC AGT GAG ACC AAG TGC ATC ATC AAG
 221  Gln Leu Asp Leu Gly Leu Trp Asp Lys Phe Ser Glu Thr Lys Cys Ile Ile Lys

920  ATC GTG GAG TTT GCC AAA CGG TTG TTT ACA AGC ATT GCT GAC ATC CAG ATC
 241  Ile Val Glu Phe Ala Lys Arg Leu Phe Thr Ser Ile Ala Asp Ile Gln Ile

980  ACT CTG CTC AAA GCT TGC CTA GAT ATC ATG CGT AGC ATC TGC ACA AGG TAC ACC
 261  Thr Leu Leu Lys Ala Cys Leu Asp Ile Met Arg Ser Ile Cys Thr Arg Tyr Thr

1040  CCA GAG CAG GAC ACC TTC TCC GAC CTT TTT ACC CTG AAC CTG ACC CAG ATG CAC
 281  Pro Glu Gln Asp Thr Phe Ser Asp Leu Phe Thr Leu Asn Leu Thr Gln Met His

1100  AAT GCC GGG TTC CCC CTC GTC GTG TTT GCT TTT ATC AGC GCC CTG CAG CTC CCC
 301  Asn Ala Gly Phe Pro Leu Val Val Phe Ala Phe Ile Ser Ala Leu Gln Leu Pro

1160  CTG GAG GAT ATG CTG CTC AAG GGG CTG CTC CTG CCA GAA GCT CTG AGG GGA GAC
 321  Leu Glu Asp Met Leu Leu Lys Gly Leu Leu Leu Pro Glu Ala Leu Arg Gly Asp

1220  CGC ATG GAC CTG GAG CCC GAG GAG AAA GTG GAC GAC AAG CAG CCA TTC TTC GAA GCC
 341  Arg Met Asp Leu Glu Pro Glu Glu Lys Val Asp Asp Lys Gln Pro Phe Phe Glu Ala

1280  CTG AGG CTG TAC CTG GCC CGG CGG CCC CAG AGC TAC ATG GCT GAG ATG AGG AGG CTA
 361  Leu Arg Leu Tyr Leu Ala Arg Arg Pro Gln Ser Tyr Met Ala Glu Met Ser Arg Leu

1340  ATG AAA ATC ACC GAC CTC TTA ATC AGC ACT CGA GGA GCC ATT ACT
 381  Met Lys Ile Thr Asp Leu Leu Ile Ser Thr Arg Gly Ala Ile Thr

1400  AAG ATG GAG CTG ATT CCA CCG CCT CCC CAC CCC AAT GCC GAG AAC CCT
 401  Lys Met Glu Leu Ile Pro Pro Pro Pro His Pro Asn Ala Glu Asn Pro

1460  ATG TTT GAG GAT CCA GAT TCC TCG TCC GAC GGT CCT GGG AAT GCC TCT AGC GAG GAT
 421  Met Phe Glu Asp Pro Asp Ser Ser Ser Asp Gly Pro Gly Asn Ala Ser Ser Glu Asp

1520  GTT CCT GGG GGC CAG CAG AAA GGG GGC CTG AAG TCC TGA CCA GGC CGA ATT
 441  Val Pro Gly Gly Gln Gln Lys Gly Gly Leu Lys Ser End Pro Ala
```

HUMAN RETINOIC ACID RECEPTORS

[amino terminal] A/B REGION FIG. 2

```
γ        MATNKERLFAAGALGPGSGYPGAGFPFAFPGALRGSPPFEMLSPSFRGLGQPDLPKEMAS
α        MASNSSSCPTPG.GHLNGYPVPPYAF.FPPML.GLSPPGALTTLQHQLPVSGYSTPSP
β              MFDCMDVL.VS..QILD.YTASPSSCMLQEKA.KAC.S..T.TEWQHRHTA

γ        LSVETQSTSSEEMVPSSPSPPPPPRVYKP 89
α        ATI....S....I...P.....L..I...  87
β        Q.I..........L...P...L........ 80
```

[DNA binding] C REGION

```
γ  90  CFVCNDKSSGYHYGVSSCEGCKGFFRRSIQKNMVYTCHRDKNCIINKVTRNRCQYCRLQK
α  88  ....Q.........A.............................................
β  81  ....Q.........A.................I.........V.................

γ      CFEVGM  155
α      ......  153 (97%)
β      ......  146 (94%)
```

[hinge] D REGION

```
γ 156  SKEAVRNDRNKKKKEVKEEGSPDSYELSPQLEELITKVSKAHQETF 201
α 154  ...S............PKPECSE..T.T.EVG...E..R....... 199
β 147  ...S............TSKQECTE...MTAE.DD.TE.IR....... 192
```

[ligand binding] E REGION

```
γ 202  PSLCQLGKYTTNSSADHRVQLDLGLWDKFSELATKCIIKIVEFAKRLPGFTGLSIADQIT
α 200  .A........N.SEQ..S..ID........S......T.....Q.....T.T......
β 193  ....................R..............................T......

γ      LLKAACLDILMLRICTRYTPEQDTMTFSDGLTLNRTQMHNAGFGPLTDLVFAFAGQLLPL
α      ...........I..............................................N.....
β      ...........I...........................................T..N.....

γ      EMDDTETGLLSAICLICGDRMDLEEPEKVDKLQEPLLEALRLYARRRRPSQPYMFPRMLM
α      ....A..............Q...Q.DR..M.........KV.V.K....R.H...K...
β      ...................Q.....T.............KI.I.K....K.H...KI..

γ      KITDLRGISTKGAERAITLKMEIPGPMPPLIREMLENPEM 421
α      ......S..A.....V.........S.....Q.....S.G 419 (84%)
β      ......S..A.....V.........S.....Q..M..S.G 412 (90%)
```

[carboxyl terminal] F REGION

```
γ 422  FEDDSSQPGPHPNASSEDEVPGGQGKGGLKSPA* 454
α 420  LDTL.G...GGGRDGGGLAP.P.SCSPS.SPSSNRSSPATHSP* 462
β 413  H.PLTPSSSGNTAEH.PSIS.SSVENS.VSQSPLVQ* 448
```

γ = GAMMA RETINOIC ACID RECEPTOR
α = ALPHA RETINOIC ACID RECEPTOR
β = BETA RETINOIC ACID RECEPTOR

Reporter: ΔM-TREp-CAT

FIG. 3A

Receptor: pRShRARγ

FIG. 3B ns with high affinity to certain specific
GAMMA RETINOIC ACID RECEPTOR This application is a continuation of application U.S. Ser. No. 08/100,039, filed Jul. 30, 1993, issued Jun. 25, 1996, as U.S. Pat. No. 5,530,094, which is in turn a divisional of U.S. Ser. No. 07/370,407, filed Jun. 22, 1989, issued Nov. 9, 1993, as U.S. Pat. No. 5,260,432, the entire contents of which are hereby incorporated by reference.

The present invention relates generally to ligand-responsive regulatory proteins and genes encoding them. More particularly, the present invention relates to a new retinoic acid receptor protein and the gene that encodes it, modification of the new retinoic acid receptor protein and gene by recombinant DNA and other genetic engineering techniques, plus uses of the new retinoic acid receptor protein and gene, both unmodified and modified.

BACKGROUND OF THE INVENTION

It is known that hormones like the glucocorticoid and thyroid hormones enter cells by facilitated diffusion. It is also known that hormones then bind to specific receptor proteins, thereby creating a hormone/receptor complex. The binding of hormone to the receptor initiates an alosteric alteration of the receptor protein. As a result of this alteration, it is believed that the hormone/receptor complex is capable of binding with high affinity to certain specific sites on the chromatin DNA. Such sites, which are referred to as hormone response elements or HRE's, modulate expression of nearby target gene promoters.

A major obstacle to further understanding of the specifics of gene regulation by exogenous inducers such as hormones has been the lack of availability of receptor proteins in sufficient quantity and purity to allow such proteins to be adequately analyzed and characterized. This same lack of availability has thwarted the use of receptors in diagnostic assays to determine the presence of exogenous inducers (e.g., the hormones) in various body fluids and tissues, as well as their use as "prototypes" for engineering chimeric receptor protein analogs.

In an effort to overcome this lack of availability of receptor proteins, scientific investigators are working to discover the genes that encode such proteins. To date several such genes have been disclosed and characterized. The cloned genes include those encoding the following receptors: glucocorticoid, mineralocorticoid, progesterone, estrogen, the two steroid-related receptors (known in the art as ERR1 and ERR2), vitamin $D_3$, thyroid, v-erb-A, E75 (Drosophilia and two retinoid receptor proteins, retinoic acid receptor alpha (RARα) and retinoic acid receptor beta (RARβ). (See Giguere, et al., (1987) regarding RARα, and Petkovich, et al., (1987) and Brand, et al., (1988) regarding RARβ.)

This disclosure describes the isolation and characterization of a cDNA encoding a third functional retinoid receptor protein that is referred to herein as the gamma retinoic acid receptor (RARγ). Like RARs alpha and beta, the new gamma retinoic acid receptor has homology with the DNA-binding and ligand-binding domains of the steroid and thyroid hormone receptors.

The retinoic acid receptor genes belong to the superfamily of genes known as the steroid hormone receptor family. All genes in this family can be divided into discrete regions or domains that are sometimes referred to as regions A/B, C, D, E, and F. See FIG. 2; also see Robertson, (1987) and Evans, (1988). The C region encodes the DNA-binding domain, the E region encodes the ligand-binding domain and the F region encodes the carboxy-terminus domain. The D region is believed to function as a "hinge". The function of the A/B (or N-terminus) region is not entirely clear; it may be involved with enhancement and repression of receptor transcription activity. See for example, Hollenberg, et al., (1988) and Oro, et al., (1988).

The present specification also discloses chimeric receptors made by "swapping" functional domains between the new gamma retinoic acid receptor and the glucocorticoid, the mineralocorticoid, the progesterone, the estrogen, the estrogen-related (ERR1 and ERR2), the vitamin $D_3$ receptor, the thyroid receptors, the v-erb-A receptor, the E75 (Drosophilia) receptor and the alpha and beta retinoic acid receptors. These chimeric receptors have hybrid functional characteristics based on the "origin" of the "parental" DNA-binding and ligand-binding domains incorporated within the chimeras. For example, if the DNA-binding domain in the chimeric receptor is the gamma retinoic acid receptor DNA-binding domain (i.e., is obtained from wild-type gamma retinoic acid receptor or is a mutant that contains the functional elements of the gamma retinoic acid DNA-binding domain), then the chimera will have DNA-binding properties characteristic of the gamma retinoic acid receptor. The same is true of the ligand-binding domain.

DESCRIPTION OF THE DRAWINGS

The drawings comprise three figures of which:

FIG. 1 is a drawing which shows the DNA nucleotide sequence and the primary protein sequence of hRARγ encoded by the EcoRI fragment harbored in pGEM-hRARγ.

FIG. 2 is a drawing that shows the amino acid comparison among the three human RARs (alpha, beta and gamma).

FIG. 3 (A and B) is composed of two blots.

DEFINITIONS

In the present specification and claims, reference will be made to phrases and terms of art which are expressly defined for use herein as follows:

As used herein, the generic term "retinoids" means a group of compounds which includes retinoic acid, vitamin A (retinol) and a series of natural and synthetic derivatives that can exert profound effects on development and differentiation in a wide variety of systems.

As used herein, the human species is identified with a lower case "h".

As used herein, "steroid hormone superfamily of receptors" refers to the class of related receptors comprised of glucocorticoid, mineralocorticoid, progesterone, estrogen, estrogen-related (ERR1 and ERR2), vitamin $D_3$, thyroid, v-erb-A, E75 (Drosophilia) and the retinoic acid receptors. See Evans (1988) and the references cited therein.

As used herein, RAR means retinoic acid receptor. The acronym hRAR means human retinoic acid receptor. hRARα refers to human retinoic acid receptor alpha. See Giguere, et al., (1987). hRARβ refers to human retinoic acid receptor beta. See Brand, et al., (1988). hRARγ refers to human retinoic acid receptor gamma.

As used herein, GR means glucocorticoid receptor. hGR means human glucocorticoid receptor.

As used herein, MR means mineralocorticoid receptor. hMR means human mineralocorticoid receptor.

As used herein, $T_3R$ means thyroid hormone receptor triiodthyronine. $T3R\alpha$ and $T_3R\beta$ refer to the alpha and beta forms of the thyroid receptor.

As used herein, ER means estrogen receptor.

As used herein, ERR means estrogen-related receptor. The acronyms, hERR1 and hERR2 refer to human estrogen-related receptors 1 and 2. These receptors are more related to steroid receptors than to the thyroid receptors, yet they do not bind any of the manor classes of known steroid hormones (Giguere, et al., 1988).

As used herein, VDR means vitamin $D_3$ receptor.

As used herein, PR means progesterone receptor.

As used herein, CAT means chloramphenicol acetyltransferase.

As used herein, CV-1 means mouse kidney cells from the cell line referred to as "CV-1". CV-1 cells are receptor-deficient cells that are useful in functional ligand identification assays.

As used herein, hormone response elements or HRE's mean short cis-acting DNA sequences (about 20 bp in size) that are required for hormonal (or ligand) activation of transcription. The attachment of these elements to an otherwise hormone-nonresponsive gene causes that gene to become hormone responsive. These sequences function in a position- and orientation-independent fashion. Unlike other transcriptional regulators, the activity of the HRE's is dependent upon the presence or absence of ligand. See Evans (1988) and the references cited therein.

As used herein, synthetic HRE's refer to HRE's that have been synthesized in vitro using automated nucleotide synthesis machines. Since the HRE's are only about 20 bp in size, they are easily synthesized in this manner. If wild-type, engineered or synthetic HREs are linked to hormone-nonresponsive promoters, these promoters become hormone responsive. See Evans (1988) and the references cited therein.

As used herein, the acronym GRE means glucocorticoid response element and TRE means thyroid receptor response element. ($TRE_p$ is a TRE that has been engineered to maximize the palindrominicity of this response element.) GRE's are hormone response elements that confer glucocorticoid responsiveness via interaction with the GR. See Payvar, et al., *Cell* 35:381 (1983) and Schiedereit, et al., *Nature* 304:749 (1983). GRE's can be used with any wild-type or chimeric receptor whose DNA-binding domain can functionally bind (i.e., activate) with the GRE. For example, since GR, MR and PR receptors can all activate GRE's, a GRE can be used with any wild-type or chimeric receptor that has a GR, MR or PR-type DNA-binding domain. TRE's are similar to GRE's except that they confer thyroid hormone responsiveness via interaction with TR. TRE's can be used with any wild-type or chimeric receptor whose DNA-binding domain can functionally bind (i.e., activate) with the TRE. Both thyroid and retinoic acid receptors can activate TRE's, so a TRE can be used with any receptor that has a TR or RAR-type DNA-binding domain.

As used herein, ligand means an inducer, such as a hormone or growth substance. Inside a cell, the ligand binds to a receptor protein, thereby creating a ligand/receptor complex, which in turn can bind to an appropriate hormone response element. Single ligands may have multiple receptors. For example, both the $T_3R_\alpha$ and the $T_3R_\beta$ bind thyroid hormone such as $T_3$.

As used herein, the phrase "DNA-binding domain" refers to that portion of the receptor protein (such as glucocorticoid, mineralocorticoid, progesterone, estrogen, estrogen-related receptors, vitamin $D_3$, thyroid, v-erb-A, E75 (Drosophilia) and the retinoic acid receptors) that binds to HRE sites on the chromatin DNA. The boundaries for these DNA-binding domains have been identified and characterized for the steroid hormone superfamily, See Evans (1988) and the references cited therein.

The DNA-binding domains of the steroid hormone superfamily of receptors consist of an amino segment varying between 66 to 68 amino acids in length. This segment contains 9 cysteine residues, one of which is the first amino acid of the segment. This first Cys residue begins a motif described as $Cys-X_2-Cys-X_{13-15}-Cys-X_2-Cys$, where X is any amino acid is residue. The DNA-binding domain invariably ends with the amino acids Gly-Met.

For convenience in the cloning procedure, between 1 and 6 amino acids residues preceding and/or following the DNA-binding domain can be switched along with the DNA-binding domain.

As used herein, the phrase "ligand-binding domain region" refers to that portion of the receptor proteins that binds to ligands such as growth substances or hormones. These boundaries of the ligand-binding domains for the steroid receptor superfamily have been identified and characterized. See Evans (1988) and the references cited therein.

Common restriction endonuclease sites must be introduced into receptor cDNA clones to allow exchange of functional domains between receptors. In any of the various receptors in the steroid receptor superfamily of genes, the first common site can be introduced immediately preceding the DNA-binding domain, the second common site immediately following it. (For example, in any of the steroid hormone superfamily, a unique NotI site can be introduced immediately preceding the region of the cDNA encoding the DNA-binding domain and a unique XhoI site can be introduced immediately following it. This divides the receptors into three functional regions or "cassettes"; (1) an N-terminus cassette, (2) a DNA-binding domain cassette, and (3) a ligand-binding domain cassette. The three regions or cassettes from any one receptor can be combined with cassettes from other receptors to create a variety of chimeric receptors.

As used herein, "mutant" DNA refers to DNA which has been genetically engineered to be different from the "wild-type" or unmodified sequence. Such genetic engineering can include the insertion of nucleotides into wild-type sequences, deletion of nucledtides from wild-type sequences, substitution of nucleotides in the wild-type sequences, or "swapping" of functional domains from one receptor to another. Receptors that have been engineered by "swapping" functional domains from one receptor to another are also referred to as chimeric or hybrid receptors. Chimeric receptors can be further engineered by insertion of nucleotides, deletion of nucleotides, substitution of nucleotides, etc.

Use of the term "substantial sequence homology" in the present specification and claims refers to DNA, RNA, or amino acid sequences that have slight and non-consequential sequence variations from the actual sequences disclosed and claimed herein and means that these sequences are within the scope of the appended claims. In this regard, the "slight and non-consequential" sequence variations mean that the homologous sequences will function in substantially the same manner to produce substantially the same compositions as the nucleic acid and amino acid compositions disclosed and claimed herein.

As used herein, the term "recombinantly produced" means made using genetic engineering techniques, not merely purified from nature.

The amino acids which comprise the various amino acid sequences appearing herein may be identified according to the following three-letter or one-letter abbreviations:

| Amino Acid | Three-Letter Abbreviation | One-Letter Abbreviation |
|---|---|---|
| L - Alanine | Ala | A |
| L - Arginine | Arg | R |
| L - Asparagine | Asn | N |
| L - Aspartic Acid | Asp | D |
| L - Cysteine | Cys | C |
| L - Glutamine | Gln | Q |
| L - Glutamic Acid | Glu | E |
| L - Histidine | His | H |
| L - Isoleucine | Ile | I |
| L - Leucine | Leu | L |
| L - Lysine | Lys | K |
| L - Methionine | Met | M |
| L - Phenylalanine | Phe | F |
| L - Proline | Pro | P |
| L - Serine | Ser | S |
| L - Threonine | Thr | T |
| L - Tryptophan | Trp | W |
| L - Tyrosine | Tyr | Y |
| L - Valine | Val | V |

The nucleotides which comprise the various nucleotide sequences appearing herein have their usual single-letter designations (A, G, T, C or U) used routinely in the art.

As used herein, bp means base pairs and kb means kilobase pairs.

DEPOSITS

Plasmid pGEM-hRARγ was deposited Jun. 22, 1989 at the American Type Culture Collection, Rockville, Md., U.S.A. (ATCC) for patent purposes. It has been accorded ATCC No. 40623.

DESCRIPTION OF THE INVENTION

In one aspect, the present invention comprises a double-stranded DNA segment wherein the plus or sense strand encodes the primary sequence of a protein that has ligand-binding and DNA-binding properties characteristic of a retinoid receptor protein referred to herein as human gamma retinoic acid receptor protein. According to this aspect of the invention, the double-stranded DNA segment is one which is capable of being expressed into human gamma retinoic acid receptor protein.

In another aspect, the invention comprises a single-stranded DNA, which is the sense strand of a double-stranded DNA coding for retinoic acid receptor gamma protein.

In another aspect, the invention comprises an mRNA made by transcription of the double-stranded DNA of the invention.

In another aspect, the invention comprises a plasmid, pGEM-hRARγ, which contains DNA encoding the human gamma retinoic acid receptor protein of the present invention (hRARγ). This plasmid has been deposited with the American Type Culture Collection for patent purposes; it has been accorded ATCC No. 40623.

In still another aspect, the invention comprises a cell, preferably a mammalian cell, transfected with a DNA coding for retinoic acid receptor gamma protein. According to this aspect of the invention, the transfected DNA is capable of being expressed in the cell, thereby increasing the amount of gamma retinoic acid receptor encoded by this DNA in the cell.

Further the invention comprises novel retinoic acid receptors made by expression of DNA coding for gamma retinoic acid receptor or translation of an mRNA transcribed from such gamma retinoic acid receptor encoding DNA. According to this aspect of the invention, the gamma retinoic acid receptors will be protein products of "unmodified" gamma retinoic acid encoding DNA's and mRNA's, or will be modified or genetically engineered gamma retinoic acid receptor protein products which, as a result of engineered mutations in the receptor DNA sequences, will have one or more differences in amino acid sequence from the corresponding naturally occurring "wild-type" gamma retinoic acid receptor proteins. Preferably these gamma retinoic acid receptors, whether "unmodified" or "engineered", will have at least about 5% (over background) of the retinoic acid binding activity and/are at least about 5% (over background) of the DNA-binding or transcription-activating activity of the corresponding naturally occurring gamma retinoic acid receptor.

Further the invention comprises chimeric receptors made by exchanging the functional domains of the gamma retinoic acid receptor with functional domains of another type. The chimeric DNA's thus produced encode chimeric receptor proteins that have functional characteristics based on the "origin" of their respective DNA- and ligand-binding domains. The chimeric receptors of the invention include double-stranded DNA's that encode the chimeric receptors, as well as single-stranded DNA's which are the sense strands of the double-stranded DNA's, and mRNA's made by transcription of the double-stranded DNA's. The invention also comprises cells, both eukaryotic and prokaryotic, that are transfected with chimeric receptors encoding DNA of the invention.

According to the preferred method for making the chimeric receptor genes and proteins of the present invention, to effect the chimeric DNA fusions, two restriction endonuclease sites are preferably introduced into each receptor DNA at comparable locations in or near the DNA-binding domains in order to divide the receptor DNA's into three functional domains or regions. (For example, a unique NotI site can be introduced immediately preceding the DNA-binding domain and a unique XhoI site can be introduced immediately following it. This divides the receptors into three functional regions or "cassettes"; (1) an N-terminus cassette, (2) a DNA-binding domain cassette, and (3) a ligand-binding domain cassette. The three regions or cassettes from the RARγ receptor can be combined with cassettes from other receptors from the steroid superfamily to create a variety of chimeric receptors.

EXPERIMENTAL ASPECTS OF THE INVENTION

Isolation of the Gamma Retinoic Acid Receptor

An oligonucleotide from RARα was labeled and used to probe a human cDNA library constructed from human tumor liver cell mRNA. Nucleotide sequence analysis of on a of the clones thug isolated revealed a long open reading frame of 454 amino acids beginning with a presumptive initiator methionine codon at position 200 as shown in FIG. 1.

RAR Amino Acid Sequence Comparison

The amino acid sequence of the newly discovered RARγ was compared with the amino acid sequences from RARα and hRARβ. The results of this comparison are shown in FIG. 2. As the drawing in the figure illustrates, remarkable identity in the amino acid sequence exists in the DNA-binding domains and in the ligand-binding domains.

Ligand Assay

Figure 3A:
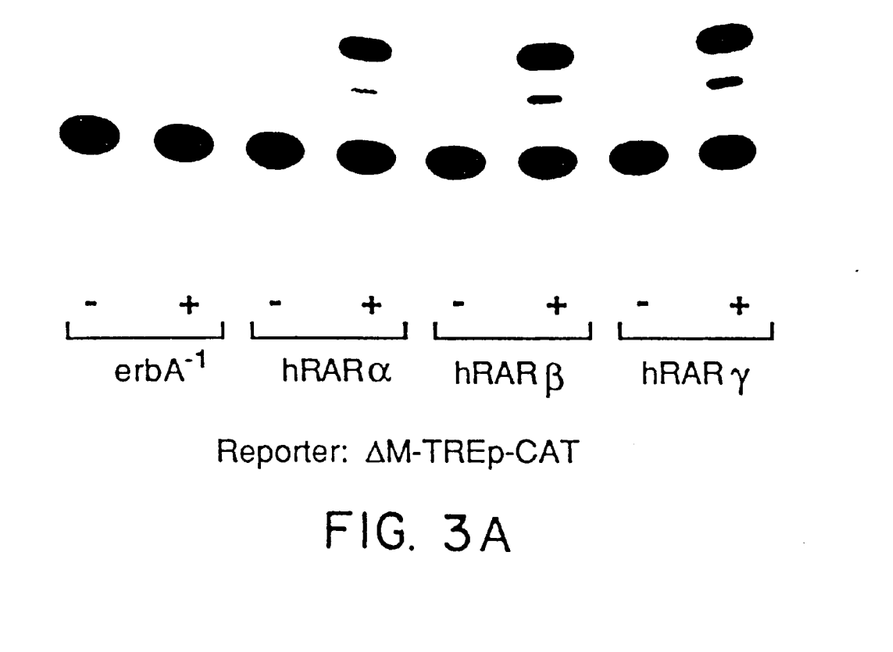
FIG. 3A shows induction of CAT activity and thus retinoic acid-dependent transactivation by the protein encoded by the cDNA insert of pGEM-hRARγ.

To assay for the ligand for the putative new retinoic acid gamma receptor protein, the NcoI-EcoRI fragment of pGEM-hRARγ was recloned in the pRS eukaryotic expression vector giving pRShRARγ. The plasmid was introduced into monkey kidney CV-1 cells via calcium-phosphate transfection together with a reporter plasmid ΔMTV-TRE$_p$-CAT. As a control, pRSerbA$^{-1}$ (encodes no protein, stands as a negative control), pRShRARα, and pRShRARβ were also examined. The transfected cells were incubated in the presence or absence of 100nM retinoic acid for 36 hours, and the induced CAT activities were analyzed by chromatography. The results indicate that a protein encoded by the NcoI-EcoRI insert transactivates through the ΔMTV-TRE$_p$ promoter in a retinoic acid dependent fashion, providing evidence that it is a functional new retinoic acid receptor. See FIG. 3A.

Response Element Specificity of hRARγ

Figure 3B:
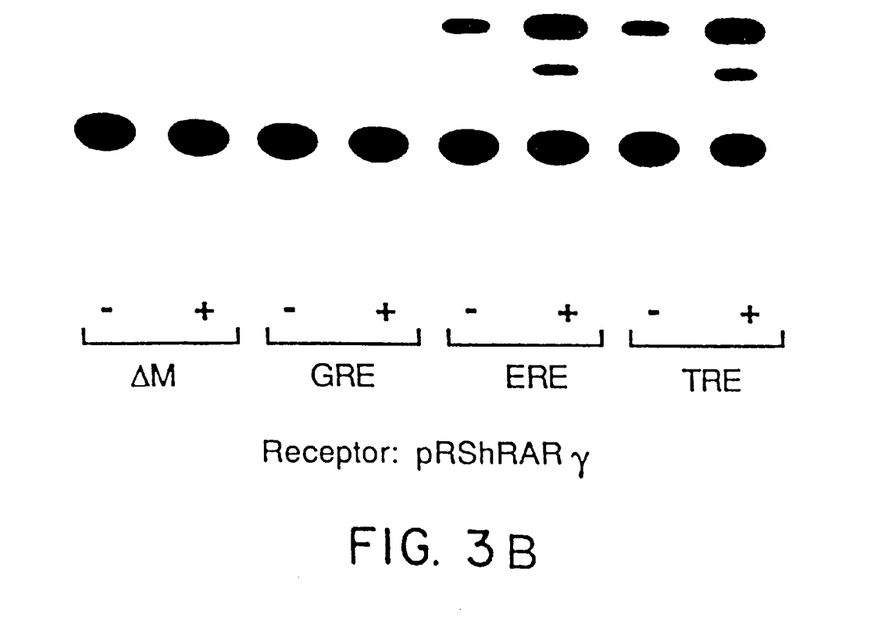
FIG. 3B shows that hRARγ recognizes ERE and TRE, but not GRE.

To assay for the hormone response elements activated by the putative new gamma retinoic acid receptor protein, the NcoI-EcoRI fragment of pGEM-hRARγ was recloned in the pRS eukaryotic expression vector giving pRShRARγ. The plasmid was introduced into monkey kidney CV-1 cells via calcium-phosphate transfection together with one of the following reporter plasmids: ΔMTV-GRE-CAT, ΔMTV-ERE-CAT, or ΔMTV-TRE-CAT, with ΔMTV-CAT as the control. As above, the transfected cells were incubated in the presence or absence of 100nM retinoic acid for 36 hours, and the induced CAT activities were analyzed by chromatography. As FIG. 3B illustrates, hRARγ recognizes ERE and TRE, but not GRE, which is consistent with the other two known human retinoic acid receptors.

Gamma Retinoic Acid Receptor Data Summary

The data disclosed herein identify the protein product encoded by the cDNA insert in pGEM-hRARγ as human gamma retinoic acid receptor based on three criteria. First, the overall structural homology that the pGEM-hRARγ gene product has with hRARα and hRARβ suggests that it is a retinoic acid receptor. Second, the RARγ receptor protein acts as a transcriptional regulator of a TRE- or an ERE-inducible reporter gene in the presence of retinoic acid. Third, the hRARγ recognizes ERE and TRE, but not GRE.

REFERENCES

The present specification refers to the following publications, each of which is expressly incorporated by reference herein.

1. Brand, N., Petkovich, M., Krust, A., and Chambon, P., "Identification of a Second Human Retinoic Acid Receptor", *Nature* 332, 850–853 (1988).
2. Evans, R., "The Steroid and Thyroid Hormone Receptor Superfamily", *Science* 240, 889–895 (1988).
3. Giguere, V., Ong, E. S., Segui, P., and Evans, R. M., "Identification of a Receptor for the Morphogen Retinoic Acid", *Nature* 330, 624–629 (1987).
4. Giguere, V., Yang, N., Segui, P., and Evans, R. M., *Nature* 331, 91- (1988).
5. Hollenberg, S. and Evans, R. M., "Multiple and Coperative Trans-Activation Domains of the Human Glucocorticoid Receptor", *Cell*, 55, 899–906 (1988).
6. Kozak, M., *Nucleic Acid Res.* 16, 8125–8148 (1987).
7. Oro, A. E., Hollenberg, S., and Evans, R. M., *Cell*, 55, 1109–1114 (1988).
8. Petkovich, M., Brand, N. J., Krust, A., and Chambon, P., "A Human Retinoic Acid Receptor Which Belongs to the Family of Nuclear Receptors", *Nature* 330, 444–450 (1987).
9. Robertson, M., "Towards a Biochemistry of Morphogenesis", *Nature* 330, 420–421 (1987).

SPECIFICATION SUMMARY

From the foregoing description, one of ordinary skill in the art can understand that the present invention provides substantially pure DNA which encodes the retinoid receptor protein referred to as the gamma retinoic acid receptor protein. The invention also provides a plasmid containing the gamma retinoic acid receptor DNA. This plasmid, pGEM-hRARγ has been deposited with the American Type culture collection for patent purposes.

The invention is also comprised of gamma retinoic acid receptor proteins, including modified functional forms thereof, expressed from the DNA (or mRNA) of the invention.

The present invention also includes chimeric hybrid receptors made by exchanging (1) the N-terminal domains, (2) the DNA-binding domains, and (3) the ligand-binding domains from hGR, hMR, ER, PR, hERR1, hERR2, T$_3$R$_α$, T$_3$R$_β$, D$_3$, v-erb-A, E75 and the alpha and beta RAR receptors with the domains of the new RARγ receptor. The chimeric receptors so constructed have DNA-binding domain and ligand-binding domain characteristics of the DNA-binding domain and ligand-binding domains of the respective "parental" receptors from which they originated.

The hRARγ DNA of the invention can be used to make the gamma retinoic acid receptor proteins, and functional modified forms thereof, in quantities that were not previously possible. The same is true of the chimeric receptors. With the quantities of gamma receptor protein available as a result of the present invention, the receptor proteins can be used to screen for gamma retinoic acid receptor-agonists or gamma retinoic acid receptor-antagonists. Availability of the gamma receptor proteins also means that they can be used in diagnostic assays to determine levels of retinoic acid present in various tissues and body fluids. Alternatively, the receptor proteins can be used to assay for levels of mRNA.

Without departing from the spirit and scope of this invention, one or ordinary skill can make various changes and modifications to the invention to adapt it to various usages and conditions. As such, these changes and modifications are properly, equitable, and intended to be, within the full range of equivalence of the following claims.

What is claimed is:

1. An isolated RARγ protein having the amino acid sequence set forth in FIG. 1 and any of the following variations of this sequence, a mutation in a DNA binding domain sequence that does not substantially effect DNA binding function or a mutation of a ligand binding domain sequence that does not substantially effect ligand binding function.

2. An isolated protein having the amino acid sequence of the hRARγ-encoding portion of clone pGEM-h hRARγ (ATCC Accession No. 40623) and any of the following variations of this sequence, a mutation in a DNA binding domain sequence that does not substantially effect DNA binding function or a mutation of a ligand binding domain sequence that does not substantially effect ligand binding function.

3. A chimeric receptor having a functional N-terminus domain, a functional DNA-binding domain, and a functional ligand-binding domain, and a ligand-binding domain, wherein the N-terminus domain of said chimeric receptor is obtained from the N-terminus domain of retinoic acid receptor-alpha (RARα), retinoic acid receptor-beta (RARβ), retinoic acid receptor-gamma (RARγ), glucocorticoid receptor (GR), mineralocorticoid receptor (MR), progesterone receptor (PR), estrogen receptor (ER), estrogen-related receptor-1 (ERR1), estrogen-related receptor-2 (ERR2), vitamin $D_3$ receptor (VDR), thyroid receptor (TR), the v-erb-A receptor, or the Drosophila E75 receptor, wherein the DNA-binding domain of said chimeric receptor is obtained from the DNA-binding domain of RARα, RARβ, RARγ, GR, MR, PR, ER, ERR1, ERR2, VDR, TR, the v-erb-A receptor, or the Drosophila E75 receptor, and wherein the ligand-binding domain of said chimeric receptor is obtained from the ligand-binding domain of RARα, RARβ, RARγ, GR, MR, PR, ER, ERR1, ERR2, VDR, TR, the v-erb-A receptor, or the Drosophila E75 receptor, wherein at least one of the domains of said chimeric receptor comprises a contiguous portion unique to RARγ.

4. A chimeric receptor according to claim 3 wherein said chimeric receptor has at least 5% of the DNA-binding or transcription-activating activity of the corresponding unmodified receptor from which the DNA-binding domain is obtained, and/or at least 5% of the ligand-binding activity of the corresponding unmodified receptor from which the ligand-binding domain is obtained.

* * * * *

UNITED STATES PATENT AND TRADEMARK OFFICE
CERTIFICATE OF CORRECTION

PATENT NO. : 6,284,870 B1  Page 1 of 1
DATED : September 4, 2001
INVENTOR(S) : Fumimaro Takaku et al.

It is certified that error appears in the above-identified patent and that said Letters Patent is hereby corrected as shown below:

<u>Column 9,</u>
Line 3, delete ", and a ligand-binding domain"

Signed and Sealed this

Tenth Day of December, 2002

JAMES E. ROGAN
*Director of the United States Patent and Trademark Office*